(12) United States Patent
Kim et al.

(10) Patent No.: US 8,885,872 B2
(45) Date of Patent: Nov. 11, 2014

(54) METHOD AND DEVICE FOR EARLY NON-INVASIVE DIAGNOSIS OF FRUIT TREE DISEASE

(75) Inventors: Jeehyun Kim, Daegu (KR); Hee Young Jung, Daegu (KR); Changho Lee, Daegu (KR); Seung-Yeol Lee, Daegu (KR)

(73) Assignee: Kyungpook National University Industry-Academic Cooperation Foundation, Daegu ( * ) Notice: Subject to any disclaimer, the term of this patent is extended or adjusted under 35 U.S.C. 154(b) by 256 days.

(21) Appl. No.: 13/583,655

(22) PCT Filed: Mar. 8, 2011

(86) PCT No.: PCT/KR2011/001575
§ 371 (c)(1),
(2), (4) Date: Nov. 13, 2012

(87) PCT Pub. No.: WO2011/111969
PCT Pub. Date: Sep. 15, 2011

(65) Prior Publication Data
US 2013/0051627 A1 Feb. 28, 2013

(30) Foreign Application Priority Data
Mar. 10, 2010 (KR) ........................ 10-2010-0021400

(51) Int. Cl.
| | |
|---|---|
| *G06K 9/00* | (2006.01) |
| *G01N 21/84* | (2006.01) |
| *G01N 21/47* | (2006.01) |
| *G01N 33/00* | (2006.01) |
| *G01B 9/02* | (2006.01) |

(52) U.S. Cl.
CPC ............ *G01B 9/02091* (2013.01); *G01N 21/84* (2013.01); *G01N 2021/8466* (2013.01); *G01N 21/4795* (2013.01); *G01N 33/0098* (2013.01)
USPC ........................................... 382/100; 356/479

(58) Field of Classification Search
CPC ............... G06K 9/00; G01B 1/00; G01N 1/00
USPC ............................ 382/110; 356/73, 479, 496
See application file for complete search history.

(56) References Cited

U.S. PATENT DOCUMENTS

| | | | |
|---|---|---|---|
| 2008/0170219 A1* | 7/2008 | Sarunic et al. ................. | 356/73 |
| 2009/0021724 A1* | 1/2009 | Mahadevan-Jansen et al. .............................. | 356/73 |

FOREIGN PATENT DOCUMENTS

KR 1020040039139 A 5/2004

OTHER PUBLICATIONS

Changho Lee et al., "The application of Optical Tomography in the Diagnosis of *Marssonina* Blotch in Apple Leaves", Journal Publication, Jun. 2012, pp. 133-140, Journal of the Optical Society of Korea vol. 16, No. 2.
Jong-Han Park et al., "Pathogenicity and Infection Mechanism of *Pseudocercospora vitis* Causing Leaf Spot Disease on Grapevine in Korea", Journal Publication, 2006, 1 page, The Korean Society of Plant Pathology.

* cited by examiner

*Primary Examiner* — Abolfazl Tabatabai
(74) *Attorney, Agent, or Firm* — Reinhart Boerner Van Deuren P.C.

(57) ABSTRACT

The present invention relates to a non-invasive early diagnostic method and device that allows an early diagnosis of *Marssonina* blotch disease, which infects apple tree leaves, before the occurrence of lesions to enable early prevention of apple *Marssonina* blotch disease. The method and device of the present invention comprise the following steps: irradiating a broadband light source on an apple tree leaf undergoing diagnosis by means of optical coherence tomography; detecting interference signals from light reflected from the apple tree leaf undergoing diagnosis and light reflected from a reference arm; signal processing the interference signals, which have been detected through optical coherence tomography by means of a signal processing unit; obtaining digital tomographic image data on the apple tree leaf undergoing diagnosis; analyzing the digital tomographic image by means of a diagnostic unit; and observing the boundary of at least two tissues, wherein the apple tree leaf undergoing diagnosis is considered to be healthy and uninfected with *Marssonina* blotch disease if the boundary between at least two tissues is clearly defined, and wherein the apple tree leaf undergoing diagnosis is considered to be infected with *Marssonina* blotch disease if the boundary between at least two tissues is not clearly defined.

12 Claims, 5 Drawing Sheets

(a)

(b)

(a)

(b)

(a)

(b)

METHOD AND DEVICE FOR EARLY NON-INVASIVE DIAGNOSIS OF FRUIT TREE DISEASE

TECHNICAL FIELD

The present invention relates to a technique for diagnosing diseases of fruit trees in a non-invasive manner using optical tomography. More particularly, the present invention relates to a method and a device for the early non-invasive diagnosis of diseases including apple *Marssonina* blotch in fruit trees before the visualization of symptoms with the naked eye, using optical tomography.

BACKGROUND ART

*Marssonina* blotch is an agriculturally significant disease which results in leaf spotting and premature defoliation in apples, roses, etc. The leaf spots in the early stage of *Marssonina* are brown or yellowish brown freckles and grow gradually, forming irregular lesions, with a yellow or green halo. Black sori are formed inside the lesions and conidiospores, when scattered from the sori by wind or rain, may settle in healthy trees and cause the disease. After infection, *Marssonina* sp., which is responsible for the outbreak of *Marssonina* leaf spot, usually has a latent period of 3~4 weeks and then concurrently appears as a lot of conidia, causing premature defoliation in July ~ August in Korea and thus significant damage for farmers.

Until now, the diagnosis of *Marssonina* blotch has been preformed with the naked eye both domestically and abroad, that is, the disease has been diagnosed just by observing the symptoms visible on the leaves. However, as stated above, because *Marssonina* blotch appears as a result of the concurrent generation of mass conidia after a long period of latency, not all fungicides are able to arrest the development of symptoms when applied after the appearance of visible symptoms.

In order to minimize the damage caused by *Marssonina* blotch, the pest must be controlled with fungicides before the outbreak of the disease. Therefore, there is a pressing need for a method providing the early diagnosis of *Marssonina* blotch.

DISCLOSURE

Technical Problem

With the aim of reducing the damage caused by apple *Marssonina* blotch, the present invention is directed to a method and a device for the early non-invasive diagnosis of apple *Marssonina* blotch before the appearance of symptoms on leaves, using optical tomography.

Technical Solution

In accordance with an aspect thereof, the present invention provides a device for the early non-invasive diagnosis of apple *Marssonina* blotch, comprising: an optical tomographic unit for generating an interference signal of a pair of backscattered light beams from both a leaf of diagnostic interest and a reference arm in an optical interferometer; a signal processor for processing the interference signal generated from the optical tomographic unit to produce data used to generate digital tomographic images; and a diagnostic unit for determining the outbreak of apple *Marssonina* blotch in the leaf.

In the device for the early non-invasive diagnosis of apple *Marssonina* blotch, the optical tomographic unit comprises: a broadband light source for generating a broad band of light for tomography; a photocoupler, comprising a first to a fourth terminal, in which the light from the light source is received through the first terminal and split into two beams through the second and the third terminals while light travelling backwards through the second and the third terminal is transmitted through the fourth terminal; a reference arm, connected to the second terminal of the photocoupler, for reflecting the light transmitted from the light source through the photocoupler; a sample arm, connected to the third terminal of the photocoupler, for irradiating the leaf of diagnostic interest with the light transmitted from the light source through the photocoupler and for receiving light backscattered from the leaf of diagnostic leaf; and a photodetector, connected to the fourth terminal of the photocoupler, for detecting the interference signal of the backscattered light from both the reference arm and the sample arm and for converting the interference signal into an electric signal.

In one preferred embodiment of the present invention, the photodetector is a balanced photodetector to increase the signal to noise-ratio (SNR). In this case, the device of the present invention further comprises an optical circulator that redirects the light which was redirected back to the broadband light source from the photocoupler towards a negative input terminal of the photodetector.

In the device for the early non-invasive diagnosis of apple *Marssonina* blotch, the function of the diagnostic unit is to analyze the tomographic image data to determine whether a boundary between the upper epidermis and the spongy parenchyma and between the spongy parenchyma and the palisade parenchyma is clearly defined on the tomographic images. A leaf is determined as being healthy when respective boundaries between the upper epidermis and the spongy parenchyma and between the spongy parenchyma and the palisade parenchyma are clearly defined and as being diseased when two or more different tissues are not clearly discriminated. For comparison purposes, a healthy leaf is used as a reference.

In accordance with another aspect thereof, the present invention provides a method for the early non-invasive diagnosis of apple *Marssonina* blotch, comprising: irradiating a leaf of diagnostic interest with the light transmitted from a light source by means of optical tomography and detecting an interference signal from light back-scattered from both the leaf of diagnostic interest and a reference arm; processing the interference signal to generate a digital tomographic image data for the leaf of diagnostic interest; analyzing the digital tomographic image data by means of a diagnostic unit to examine whether a boundary between two or more different histological tissues is clearly defined, wherein the leaf of diagnostic interest is determined as being healthy when a boundary between two or more different histological tissues is clearly defined and as being diseased when two or more different histological tissues are not clearly discriminated.

In the method for the early non-invasive diagnosis of apple *Marssonina* blotch, the digital tomographic image data is processed to extract a boundary between different histological tissues and a decision is made as to whether the boundary between the different histological tissues is clearly defined.

Advantageous Effects

As described above, the present invention utilizes the histological modification induced by pathogenic infection, which creates a histological difference between healthy and diseased leaves. Tomographic images obtained from leaves of diagnostic interest by optical tomography are compared to those from a healthy reference to determine the outbreak of a disease before the appearance of symptoms on the surface of the leaves. Accordingly, diseases in fruit trees can be diagnosed early on, thus significantly reducing the damage done as the disease progresses. In addition, optical tomography allows images to be obtained in a non-invasive manner, thereby enabling diseases including apple *Marssonina* blotch to be diagnosed in their early stages in a simple manner.

BEST MODE

Figure 1:
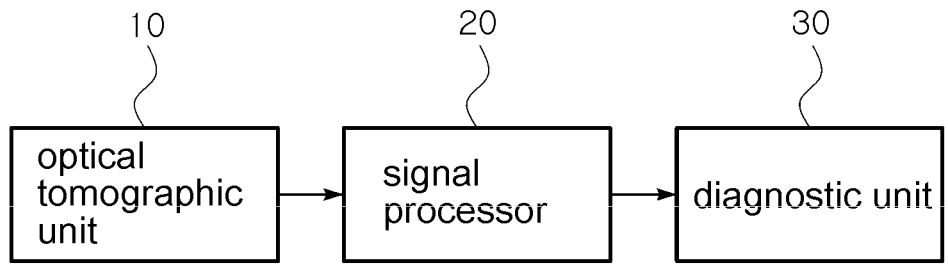
FIG. 1 is a schematic block diagram showing a structure of the device for the early non-invasive diagnosis of apple *Marssonina* blotch according to the present invention.

Below, a description will be given of preferred embodiments of the present invention in conjunction with the accompanying drawings. Throughout the accompanying drawings, the same reference numerals are used to designate the same or similar components. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted.

Unless the context clearly demands otherwise, throughout the description and the claims, the term "connected to" is intended to encompass the situation of "'connected indirectly to' through an element" as well as "connected directly to". Unless the context clearly requires otherwise, throughout the description and the claims, the words "comprise," "comprising," and the like are to be construed in an inclusive sense as opposed to an exclusive or exhaustive sense, that is to say, in the sense of "including, but not limited to."

The present invention addresses the early diagnosis of *Marssonina* blotch on the basis of the cytostructural morphogenesis which is significantly different from healthy to diseased leaves due to SAR (systemic acquired resistance), which is a defense mechanism against the infection of plant pathogens. The diagnosis is performed by reaching a decision about the infection of the pathogen from tomograms, taken from leaf tissues, which show structural differences between healthy and diseases leaves. The present invention allows *Marssonina* blotch to be diagnosed prior to the visual appearance of lesions on the leaves. This will be more clearly understood from the following description.

With reference to FIG. 1, a device for the early non-invasive diagnosis of *Marssonina* blotch according to the present invention is structurally depicted in a block diagram.

As shown in FIG. 1, the device for the early non-invasive diagnosis of *Marssonina* blotch according to the present invention comprises an optical tomographic unit 10, a signal processor 20, and a diagnostic unit 30.

The optical tomographic unit 10 is adapted to take tomographic images from leaves of diagnostic interest in a non-invasive manner without dissection and is used herein to irradiate leaves with light from a broadband light source to generate interference signals mediated by a Michelson interferometer from which the tomographic images of the leaves can be configured. In more detail, the optical tomographic unit 10 works on the basis of OCT (optical coherence tomography). So long as it is OCT, any OCT, such as time-domain OCT, spectral-domain OCT, swept source OCT, etc. may be employed in the present invention.

In one preferred embodiment of the present invention, the optical tomographic unit 10 is implemented in a time-domain OCT manner.

The signal processor 20 is designed to process the interference signals generated from the optical tomographic unit 10 to produce tomographic image data of the leave of diagnostic interest. In greater detail, the signal processor 20 outputs tomographic image data after performing DC filtering, envelope detection and digital conversion.

Functioning to analyze the tomographic structures of the leaves of diagnostic interest through the tomographic image data supplied from the signal processor 20, the diagnostic unit 30 diagnoses the infection of *Marssonina*. In detail, according to one preferred embodiment of the present invention, the diagnostic unit 30 can decide whether a leaf of diagnostic interest is diseased or not by storing a tomographic image taken from a normal healthy leaf as a reference image and comparing a tomographic image obtained from the leaf of diagnostic interest with the reference image. In another preferred embodiment of the present invention, the diagnosis may be achieved by definitively discriminating the upper epidermis from the palisade parenchyma on the tomographic image taken from the leaf of diagnostic interest. The diagnostic unit 30 determines the leaf of diagnostic interest to be a healthy leaf when the plant tissues are definitively discriminated from each other, and as diseased if not. The basis of this diagnosis may be understood from the following experimental results.

Further, the diagnostic unit 30 functions to analyze the digital tomographic image data to calculate an average peak intensity of each tissue layer of histological tissues, thereby determining that the leaf is a diseased leaf when the average intensity for each layer is not distinct compared to a background signal.

The diagnosis of the diagnostic unit 30 may be implemented by operating a diagnosis program installed on a personal computer (PC).

Figure 2:
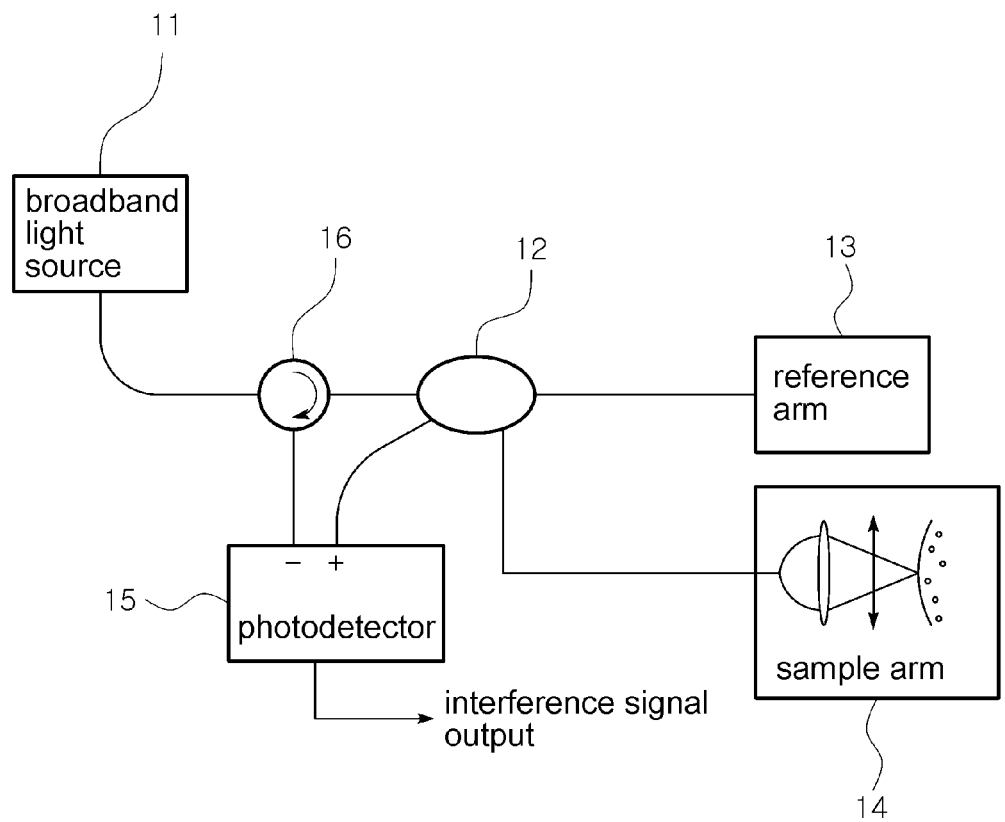
FIG. 2 is a schematic block diagram showing a structure of an optical tomographic unit in the device for the early non-invasive diagnosis of apple *Marssonina* blotch according to the present invention.

A detailed description of the optical photographic unit 10 may be given with reference to FIG. 2.

FIG. 2 is a block diagram showing a detailed structure of the optical tomographic unit 10 in a device for the non-invasive diagnosis of *Marssonina* blotch in accordance with an embodiment of the present invention.

As shown in FIG. 2, the optical tomographic unit 10 comprises a broadband light source 11, a photocoupler 12, a reference arm, a sample arm 14, a photodetector 15, and optionally an optical circulator 16. There are connections formed among the broadband light source 11, the photocoupler 12, the reference arm 13, the sample arm 14, the photodetector 15, and optionally the optical circulator 16 via an optical fiber.

The broadband light source 11 generates a broad band of light for tomography purposes. The broadband light source 11 according to one embodiment of the present invention may be an SLED (super luminescence emitting diode) centered at 1310 nm with a full length at half maximum of 150 nm.

The photocoupler 12 functions to split the incident light into two light beams which are directed to the reference arm 13 and the sample arm 14, respectively, and inversely to couple the two reflected beams incident from the reference arm 13 and the sample arm 14 and transmit the coupled light beams to the photodetector 15.

When light is incident from the photocoupler 12 on the reference arm 12, the arm 12 reflects the light, as it is, to the photocoupler 12. In one embodiment of the present invention, the reference arm 13 is embodied by an RSOD (Rapidly Scanning Optical Delayline) which provides a variable optical path length. The RSOD consists of a diffraction grating with 600 grooves/mm and a galvo-scanner for changing the path length at 300 Hz.

The sample arm 14 is adapted to focus the light coming from the photocoupler 12 which strikes a leaf of interest and to transmit the backscattered light from the leaf back into the photo coupler 12. The galvo-scanner in the sample arm 12 is used to generate the B-mode scan. In the sample arm 12, the light is focused by an objective lens with an 15 mm focal length. The B-scanning range is 2 mm.

The photodetector 15 detects interference signals incident from the photocoupler 12 in which backscattered light from the reference arm 13 and the sample arm 14 of the Michelson interferometer are coupled and converts the signal to an electrical signal (voltage). Interference signals of the two backscattered light beams from the reference arm 13 and the sample arm 14 are observed when the path length between the reference arm 13 and the sample arm 14 (the optical path length) matches the coherence length of the source.

In one preferred embodiment of the present invention, the photodetector 15 is a balanced photodetector. In this case, the device of the present invention further comprises an optical circulator 16 that redirects the light that was redirected back to the broadband light source from the photocoupler 12 towards a negative input terminal of the photodetector 15. In this construction, the photodetector increases the signal to noise ratio of the interference signal that was detected.

In the optical tomographic unit 10, the light generated from the broadband light source 11 is split into two beams by the photocoupler 12 which are incident on the reference arm 13 and the sample arm 14, respectively. The light incident on the reference arm 13 is reflected by a reference mirror (not shown) while the light incident on the sample arm 14 is reflected by interfaces of the leaf of diagnostic interest. These backscattered light beams are directed backwards into the photocoupler 12.

When the two backscattered light beams from the reference arm 13 and the sample 14 are coupled back to the photocoupler 12, a difference between reflection coefficients of the two backscattered beams produces an interference signal.

The interference signal is detected by the photodetector 15 and converted into an electric signal. Two- or three-dimensional images of the leaf of diagnostic interest can be obtained by measuring interference signals generated when the focal position of the focusing lens (not shown) in the sample arm 14 is moved in a lateral direction along the surface of the leaf while changing the distance between a collimating lens and a reference mirror (not shown) in the reference 13.

Figure 3:
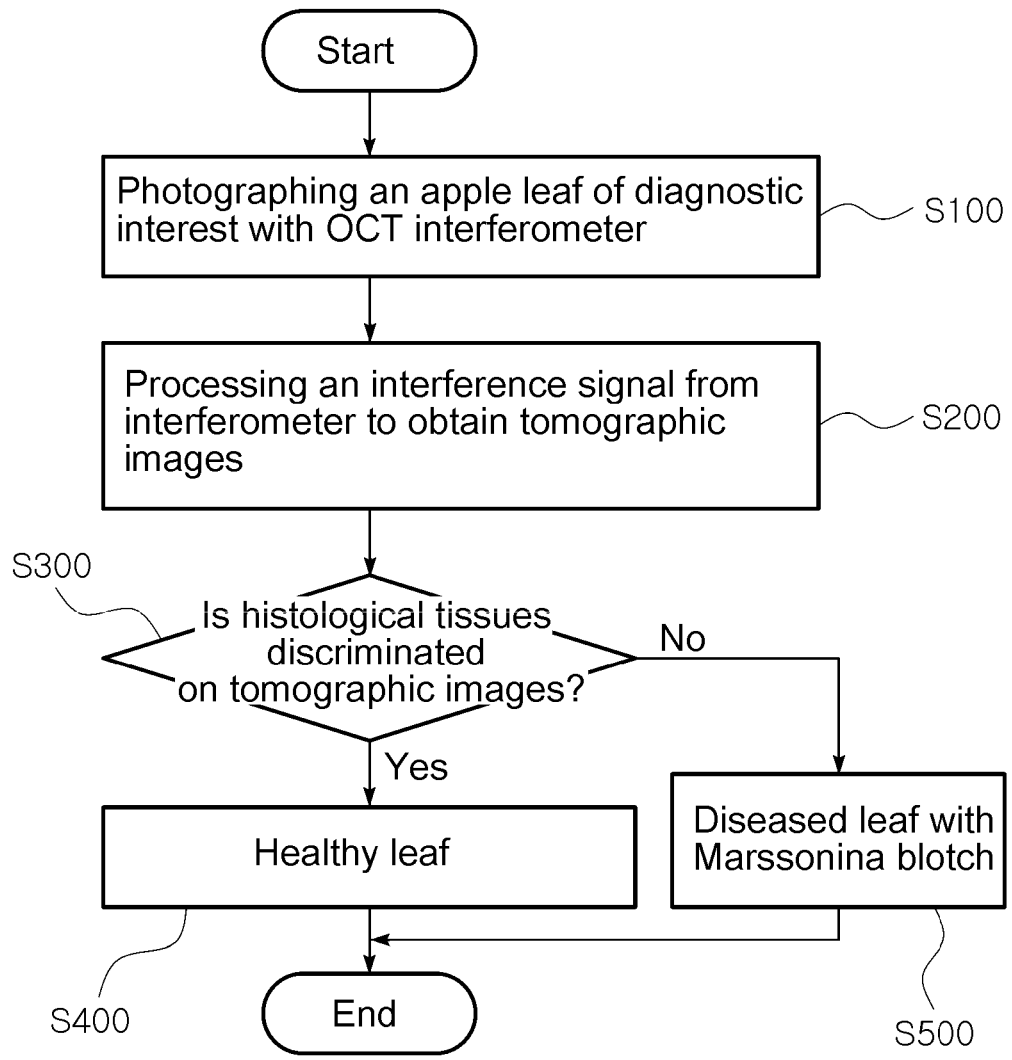
FIG. 3 is a flow chart showing a method for the early non-invasive diagnosis of apple *Marssonina* blotch according to the present invention.

Referring to FIG. 3, a flow chart is provided to illustrate a method of providing the early non-invasive diagnosis of apple *Marssonina* blotch. The following description of the diagnostic procedure for diagnosing apple *Marssonina* blotch using the device of the present invention will be further the understanding of the diagnostic procedure.

As shown in FIG. 3, the method for the early non-invasive diagnosis of apple *Marssonina* blotch starts with photographing an apple leaf of interest using optical tomography (S100). Preferably, the optical tomography utilizes a Michelson interferometer. In detail, the optical tomography used in the present invention is preferably based on OCT (optical coherence tomography) or 0CM (optical coherence tomography).

Then, the optical interference signal from the interferometer is processed to obtain tomographic image data (S200). In greater detail, this step (S200) may be performed by carrying out DC filtering, envelope detection and digital conversion on the optical interference signals.

Once obtained from an apple leaf of diagnostic interest, the digital tomographic image data is analyzed to see whether the leaf tissues can be definitively discriminated from each other (S300). In detail, a decision is made about whether a boundary between an upper epidermis and a palisade parenchyma is clearly defined on the digital tomographic image. This can be achieved by extracting boundaries between different histological tissues using image processing and examining whether there are two or more boundaries between the different histological tissues.

If the two tissues are definitively defined, the leaf of diagnostic interest is determined to be healthy (S400).

On the other hand, when the boundary is ambiguous compared to the image of a reference healthy leaf, the objective leaf is determined to have been infected with apple *Marssonina* blotch (S500).

The device and the method for the early non-invasive diagnosis of *Marssonina* blotch can be implemented and are reliable for diagnosis as the following experimental results will demonstrate.

In this experiment, a time-domain OCT device was employed. The OCT light source was an SLED having a center wavelength of 1300 nm with full width at half maximum of 150 nm. An RSOD was used in the reference arm and consisted of a diffraction grating with 600 grooves/mm and a galvo-scanner that changes the path length at 300 Hz. The light in the sample arm is focused by an objective lens with a 15 mm focal length. The galvo-scanner was used in the sample arm to generate B-scan. The B-scanning range in the time domain OCT device was 2 mm. In addition, the photodetector was a balanced detector (Thorlabs). The backscattered light of the photocoupler was redirected toward a minus input terminal of the photodetector by the optical circulator. In this experiment, the sampling rate was 10,000,000 Hz, the number of A-scans per tomographic image was 200, and the number of samples per single depth scan (A-scan) was 15,000. The axial resolution of the time-domain OCT used in the experiment was calculated to be 4.5 μm, but actually measured to be 6 μm.

Figure 4:
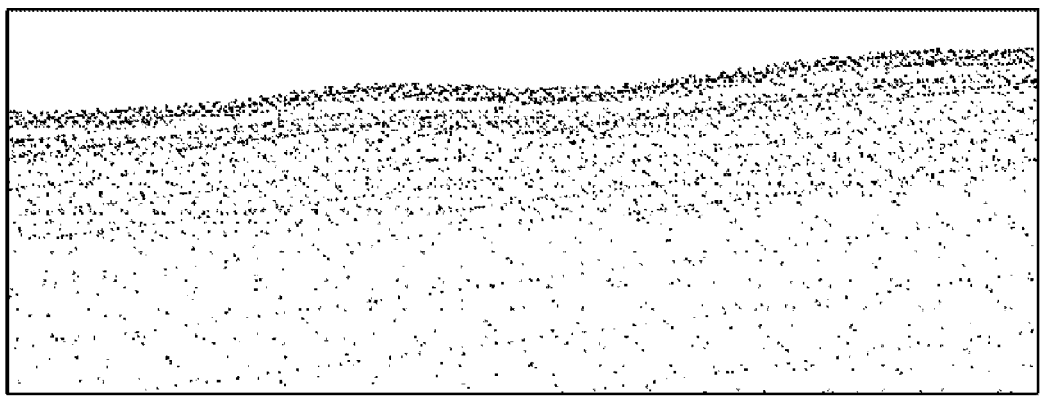
FIG. 4 shows histological tissues of a healthy apple leaf in an optical tomographic image (a) and an electron microphotograph (b).
Figure 4:
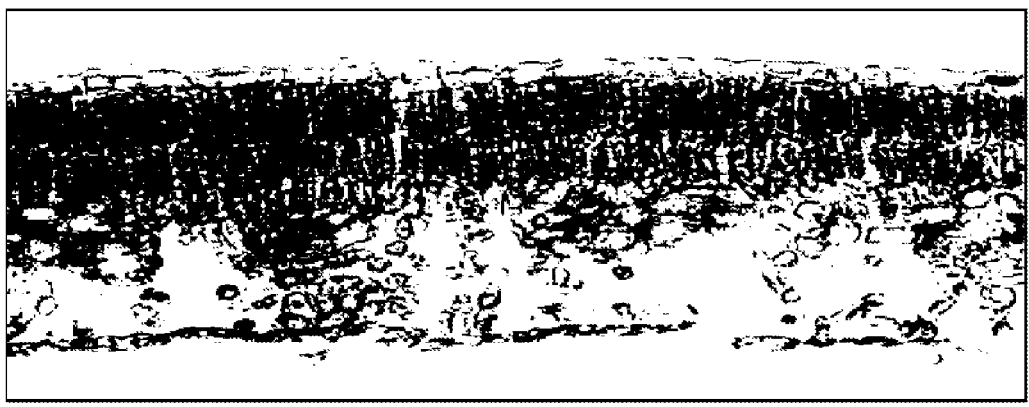
Figure 5:
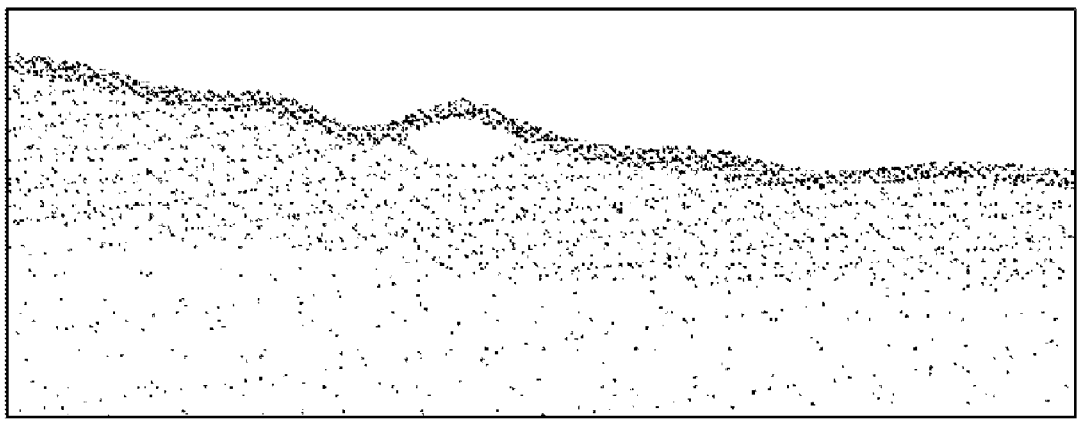
FIG. 5 shows histological tissues of a *Marssonina* blotch-diseased leaf in an optical tomographic image (a) and an electron microphotograph (b), which have been taken from the site of the same lesion of the leaf.
Figure 5:
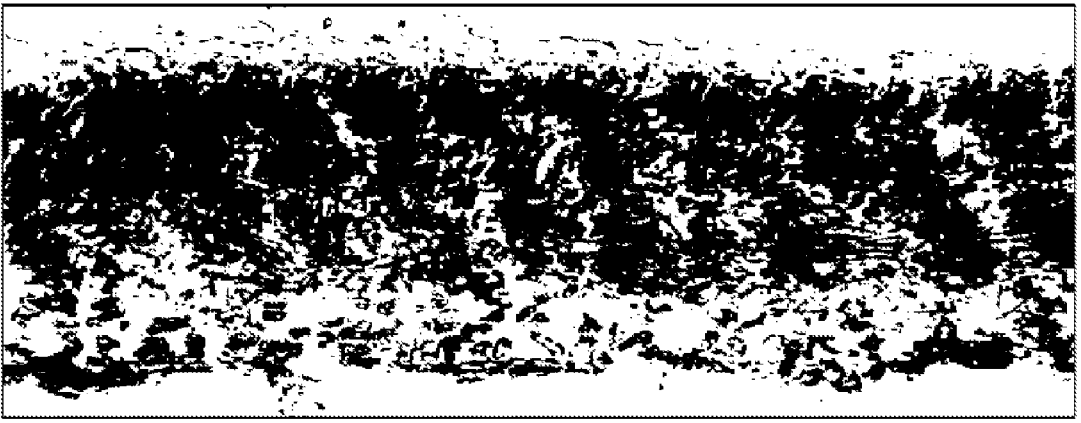
Figure 6:
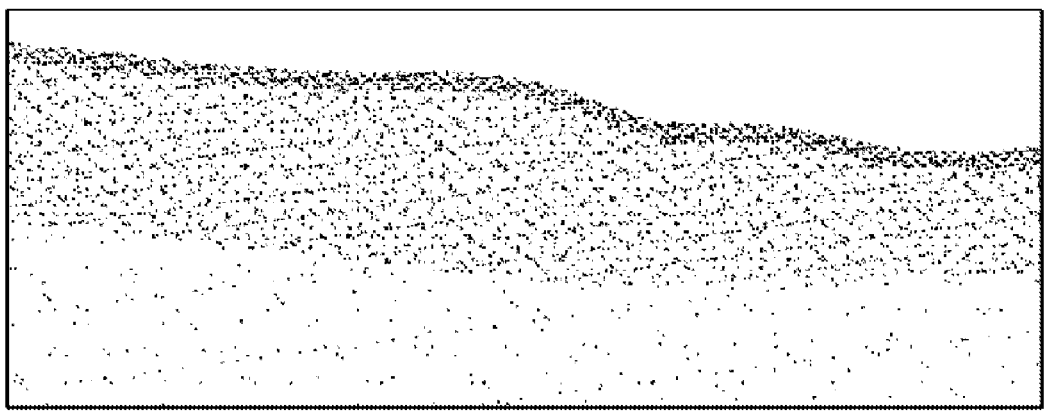
FIG. 6 shows histological tissues of the *Marssonina* blotch-diseased leaf of FIG. 5 in an optical tomographic image (a) and an electron microphotograph (b), which have been taken from a non-lesion site distant from the lesion site.
Figure 6:

Turning to FIGS. 4 to 6, comparisons have been made between OCT images and electron microphotographs taken from healthy and *Marssonina*-infected leaves of the same apple tree.

With reference to FIG. 4, there are a tomographic image (a) and a microphotograph (b) taken from a healthy apple leaf. As shown in FIG. 4a, the tomographic image provides clear boundaries between different tissues, discriminating three layers including the upper epidermis, the spongy parenchyma and the palisade parenchyma. This definitive histological discrimination is also visible in the electron microphotograph of FIG. 4b taken from the same leaf.

With reference to FIG. 5, the histology of a lesion site of a leaf diseased with *Marssonina* blotch is shown in an OCT image (a) and in an electron microphotograph (b). As is understood from the tomographic image of FIG. 5a, the upper epidermis cannot be clearly discriminated from the palisade parenchyma in the lesion site. The electron microphotograph of the same lesion site demonstrates that the histological structures of the upper epidermis and palisade parenchyma are destroyed, with loss of the ability to discriminate between the two.

With reference to FIG. 6, an OCT image and an electron microphotograph of the diseased leaf of FIG. 5, taken from a non-lesion site (e.g., 2.9 mm) distant from the lesion site, are provided. As seen in FIG. 6a, only the upper epidermis can be discriminated and other internal histological structures have been destroyed as in FIG. 5, when a leaf is diseased, although no apparent symptoms are visible on the surface of the leaf. This is confirmed by the electron microphotograph of FIG. 6b.

That is, once a leaf is afflicted with *Marssonina* blotch, its internal structures break down to the extent that they cannot be discriminated definitively even when the symptom has developed internally and not externally. The internal tissues start to collapse as the pathogen develops within the leaf although no symptoms are visible.

Taken together, the data obtained above demonstrates that the device and the method for the early non-invasive diagnosis of apple *Marssonina* blotch make it possible to accurately diagnose apple *Marssonina* blotch using OCT images. It is also apparent that *Marssonina* infection can be detected before symptoms can be seen with the naked eye.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and device within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

INDUSTRIAL APPLICABILITY

As described hitherto, OCT images of fruit trees which can be obtained without invading the trees according to the device and method of the present invention allow the detection of a histological modification induced by pathogenic infection, thereby diagnosing a disease in its early stage in fruit trees. Accordingly, the early diagnosis using the device and the method of the present invention will make a great contribution to the agricultural field.

The invention claimed is:

1. A device for early non-invasive diagnosis of a fruit tree disease, comprising:

an optical tomographic unit for generating an interference signal of a couple of backscattered light beams from both a leaf of diagnostic interest and a reference arm in an optical interferometer;

a signal processor for processing the interference signal generated from the optical tomographic unit to generate data used to produce digital tomographic images; and a diagnostic unit for determining outbreak of the disease, including apple *Marssonina* blotch, in the leaf.

2. The device of claim 1, wherein the optical tomographic unit comprises:

a broadband light source for generating a broad band of light for tomography;

a photocoupler, comprising a first to a fourth terminal, in which the light from the light source is received through the first terminal and split into two beams by the second and the third terminal while light directed backwards through the second and the third terminal is transmitted through the fourth terminal;

a reference arm, connected to the second terminal of the photocoupler, for reflecting the light transmitted from the light source through the photocoupler;

a sample arm, connected to the third terminal of the photocoupler, for irradiating the leaf of diagnostic interest with the light transmitted from the light source through the photocoupler and for receiving light backscattered from the leaf of diagnostic leaf; and a photodetector, connected to the fourth terminal of the photocoupler, for detecting the interference signal of the backscattered light from both the reference arm and the sample arm and for converting the interference signal into an electrical signal.

3. The device of claim 2, wherein the photodetector is a balanced detector having a plus input terminal and a minus input terminal and the optical tomographic unit further comprises an optical circulator for redirecting a light beam toward a minus terminal of the potodetector, said light beam being redirected back to the broadband light source from the photocoupler.

4. The device of claim 1, wherein the diagnostic unit functions to analyze the tomographic image data to determine whether the leaf is a healthy leaf when two or more histological tissues can be discriminated on the tomographic image and whether the leaf is a diseased leaf when two or more histological tissues cannot be discriminated on the tomographic image.

5. The device of claim 4, wherein the diagnostic unit functions to determine outbreak of the disease on the plant leaf by extracting boundaries between different histological tissues and examining whether two or more boundaries between the different histological tissues are present.

6. The device of claim 5, wherein the diagnostic unit functions to analyze the tomographic image data and determine that the leaf is a diseased leaf when the boundaries between different histological tissues are ambiguous compared to an image of a reference healthy leaf.

7. The device of claim 4, wherein the diagnostic unit functions to analyze the digital tomographic image data to calculate an average peak intensity of each tissue layer of histological tissues, thereby determining that the leaf is a diseased leaf when the average intensity for each layer is not distinct compared to a background signal.

8. The device of claim 1, wherein the interferometer is based on OCT (optical coherence tomography) or OCM (optical coherence microscopy) and the optical tomographic unit takes an image at a high resolution without damaging a plant.

9. A method for early non-invasive diagnosis of a fruit plant disease, comprising:
    irradiating a leaf of diagnostic interest with light transmitted from a light source by means of optical tomography and detecting an interference signal from light backscattered from both the leaf of diagnostic interest and a reference arm;
    processing the interference signal to produce digital tomographic image data for the leaf of diagnostic interest;
    analyzing the digital tomographic image data by means of a diagnostic unit to examine whether a boundary between two or more different histological tissues is clearly defined,
    wherein the leaf of diagnostic interest is determined to be healthy when a boundary between two or more different histological tissues is clearly defined and as being diseased when a boundary between two or more different histological tissues is not clearly defined.

10. The method of claim 9, wherein the analyzing the image data to examine whether a boundary is clearly defined is conducted by extracting a boundary between different histological tissues using image processing, and examining whether there are two or more boundaries between the different histological tissues.

11. The method of claim 9, wherein the digital tomographic image data is analyzed to determine that the leaf of diagnostic interest is diseased when the boundaries are ambiguous compared to an image of a reference healthy leaf.

12. The method of claim 9, wherein the digital tomographic image data is analyzed to calculate an average peak intensity of each tissue layer of histological tissues, thereby determining the leaf to be a diseased leaf when the average intensity for each layer is not distinct compared to a background signal.

* * * * *